United States Patent
McBrady et al.

(10) Patent No.: US 11,380,438 B2
(45) Date of Patent: Jul. 5, 2022

(54) RESPIRATION-VOCALIZATION DATA COLLECTION SYSTEM FOR AIR QUALITY DETERMINATION

(71) Applicant: Honeywell International Inc., Morris Plains, NJ (US)

(72) Inventors: Adam Dewey McBrady, Minneapolis, MN (US); Stephan Bork, Murphy, TX (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 259 days.

(21) Appl. No.: 15/717,661

(22) Filed: Sep. 27, 2017

(65) Prior Publication Data

US 2019/0095586 A1 Mar. 28, 2019

(51) Int. Cl.
*G10L 25/66* (2013.01)
*G10L 25/60* (2013.01)
(Continued)

(52) U.S. Cl.
CPC .............. *G16H 40/63* (2018.01); *A61B 5/08* (2013.01); *A61B 5/411* (2013.01); *A61B 5/4803* (2013.01);
(Continued)

(58) Field of Classification Search
CPC ........ G16H 10/60; G16H 50/30; G16H 10/20; G16H 40/20; G16H 50/20; G06F 19/3418;
(Continued)

(56) References Cited

U.S. PATENT DOCUMENTS 6,288,646 B1 * 9/2001 Skardon .............. G06F 19/3418
340/627
6,466,133 B1 * 10/2002 Skardon ................. G16H 40/63
340/627
(Continued)

FOREIGN PATENT DOCUMENTS

| CN | 107438398 A | * 12/2017 | ........... A61B 5/0002 |
| WO | WO-2016/014135 A1 | 1/2016 | |
| WO | WO-2017032873 A2 | * 3/2017 | ........... A61B 5/7275 |

OTHER PUBLICATIONS

Pelley, Brad J.; Occupational health and the analytical and numerical modeling of airflow patterns in the industrial environment; Memorial University of Newfoundland (Canada). ProQuest Dissertations Publishing, 2003. MQ99103 (Year: 2003).*

*Primary Examiner* — Hiep V Nguyen
(74) *Attorney, Agent, or Firm* — Alston & Bird LLP

(57) ABSTRACT

Apparatus and associated methods relate to the determination of local environmental air quality by processing data from a local device sensing a user's respiration-vocalization. In an illustrative example, respiration-vocalization for a CPAP user may be sensed by an airflow and/or air pressure sensor. Respiratory disturbance events, such as coughing, for example, may be detected. The sensed events, converted to respiration-vocalization data, may be collected to estimate the environmental air quality and/or particle density around the user. Some examples may estimate specific allergen concentrations by correlating user respiration-vocalization data with the respiration-vocalization data from users/patients with known airborne particle sensitivities. In some embodiments, regional environmental air quality data may be compared with respiration-vocalization data to produce local environmental air quality results. Various results may advantageously indicate specific allergen conditions in an
(Continued)

area based on monitoring of a population of users of CPAP machines or other devices in widespread use.

20 Claims, 8 Drawing Sheets

(51) Int. Cl.

| | | |
|---|---|---|
| *G16H 10/60* | (2018.01) | |
| *G16H 50/20* | (2018.01) | |
| *A61B 5/00* | (2006.01) | |
| *G16H 40/63* | (2018.01) | |
| *A61B 5/08* | (2006.01) | |
| *A61B 7/00* | (2006.01) | |
| *G10L 25/90* | (2013.01) | |
| *A61B 5/087* | (2006.01) | |

(52) U.S. Cl.
CPC ............ *A61B 5/6898* (2013.01); *A61B 7/003* (2013.01); *G10L 25/60* (2013.01); *G10L 25/66* (2013.01); *G16H 10/60* (2018.01); *G16H 50/20* (2018.01); *A61B 5/087* (2013.01); *A61B 5/0823* (2013.01); *A61B 2560/0242* (2013.01); *A61B 2562/0204* (2013.01); *G10L 25/90* (2013.01)

(58) Field of Classification Search
CPC .... G06F 19/00; G06F 19/325; G06F 19/3456; A61B 5/08; A61B 5/0823; A61B 5/087; A61B 5/411; A61B 5/4803
USPC .......................................................... 705/3
See application file for complete search history.

(56) References Cited

U.S. PATENT DOCUMENTS

| | | |
|---|---|---|
| 9,055,861 B2 | 6/2015 | Oh et al. |
| 9,070,357 B1 | 6/2015 | Kennedy et al. |
| 2002/0010587 A1* | 1/2002 | Pertrushin .............. G10L 17/26 704/275 |
| 2002/0091334 A1* | 7/2002 | Weber ...................... A61B 5/08 600/529 |
| 2002/0186137 A1* | 12/2002 | Skardon ................. G16H 40/63 340/573.1 |
| 2005/0119586 A1* | 6/2005 | Coyle .................. A61B 5/0806 600/538 |
| 2009/0112114 A1* | 4/2009 | Ayyagari ............... A61B 7/003 600/529 |
| 2015/0142492 A1* | 5/2015 | Kumar ................... G10L 25/66 705/7.15 |
| 2016/0256097 A1 | 9/2016 | Manautou et al. |
| 2017/0112430 A1 | 4/2017 | Hampton et al. |

\* cited by examiner

RESPIRATION-VOCALIZATION DATA COLLECTION SYSTEM FOR AIR QUALITY DETERMINATION

TECHNICAL FIELD

Various embodiments relate generally to sensing allergens and/or environmental quality.

BACKGROUND

A typical living environment may contain various particles. Some particles may be airborne, some may be foodborne, and still others may be waterborne. Airborne particles may include various pollens, dust or pollutants. Foodborne particles may include various chemicals or compounds. Waterborne particles may include some of the same particles found in the air and in food.

In some instances, the human body may react to harmless particles. For instance, certain pollens may be innocuous to people with normal and healthy immune systems. However, in some individuals, when particles are ingested, or when particles come in contact with skin or mucus membranes (e.g., eyes, nose, throat) an allergic reaction may occur. In some instances, the reaction may be serious or aphylactic. In an exemplary aspect, humans with airborne allergies may possess selective particle sensitivities. For example, someone allergic to ragweed pollen, may not be allergic to tree pollen. Some people that suffer from allergies may not be aware of the specific particles that cause the allergic reaction.

Various national weather services may track various airborne particles. People with allergies to various airborne particles may leverage these services to become aware of incipient allergy reactions. When these services indicate the presence of various airborne particles, those with allergies to those particles may take precautionary measures such as closing windows or avoiding certain outdoor activities.

SUMMARY

Apparatus and associated methods relate to the determination of local environmental air quality by processing data from a local device sensing a user's respiration-vocalization. In an illustrative example, respiration-vocalization for a CPAP user may be sensed by an airflow and/or air pressure sensor. Respiratory disturbance events, such as coughing, for example, may be detected. The sensed events, converted to respiration-vocalization data, may be collected to estimate the environmental air quality and/or particle density around the user. Some examples may estimate specific allergen concentrations by correlating user respiration-vocalization data with the respiration-vocalization data from users/patients with known airborne particle sensitivities. In some embodiments, regional environmental air quality data may be compared with respiration-vocalization data to produce local environmental air quality results. Various results may advantageously indicate specific allergen conditions in an area based on monitoring of a population of users of CPAP machines or other devices in widespread use.

Apparatus and associated methods relate to receiving user-specific respiration-vocalization data to detect various changes associated with a respiratory reaction to environmental quality. In an illustrative embodiment, the user-specific respiration-vocalization data may be sampled in short snippets, for example, from the microphone in a smart phone. The system may correlate the respiration-vocalization changes with specific allergen response data from patients with known sensitivities. The system may further process the correlations to determine various user-specific irritant sensitivities. The data correlation may be analyzed within the local device and/or in a network server (e.g., cloud server, Internet server). Airborne particles present with respect to location, for example, may be determined within the network server and may produce environmental quality maps. In some implementations, particle intensity charts or maps may be produced. In some examples, the respiration-vocalization data may be analyzed in the user device, where the user device is operable to detect respiration-vocalization changes, such as hoarseness, from a predetermined respiration-vocalization baseline. Some embodiments may be a respiration-vocalization data acquisition system (RVDAS) for air quality determination.

Various embodiments may achieve one or more advantages. For example, some embodiments may provide allergy sufferers with a diagnosis of specific allergens that may be causing sensitivities. Higher accuracy and/or detail of regional pollen intensities, environmental data, air quality and/or maps may be facilitated through employment of the RVDAS. The respiration-vocalization data from the RVDAS may be used to facilitate higher accuracy maps without added environmental sensors or hardware. Users may acquire environmental quality results data from the RVDAS in the form of irritant charts and intensity maps, by executing an application (app) on one or more local devices. As more users with known airborne irritant sensitivities add data to the system database, the more accurate the system becomes at identifying specific allergens for specific users, and the more confidence can be placed on the results. Further, as more accurate and higher resolution airflow and pressure sensors are employed, various irritants causing similar symptoms may be differentiated, which may allow proper and more effective medications or therapy to be prescribed.

In various smart phone embodiments, the user need not manually activate the RVDAS to turn it on. The RVDAS may automatically activate whenever the user employs his voice to interact with the smart phone. Further, the user's smart phone may locally store baseline data (e.g., tone, frequency, pitch) of a user's normal voice. This local baseline data may also be processed locally on the smart phone, which may advantageously provide a level of security, and facilitate detection of sudden voice changes.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 1:
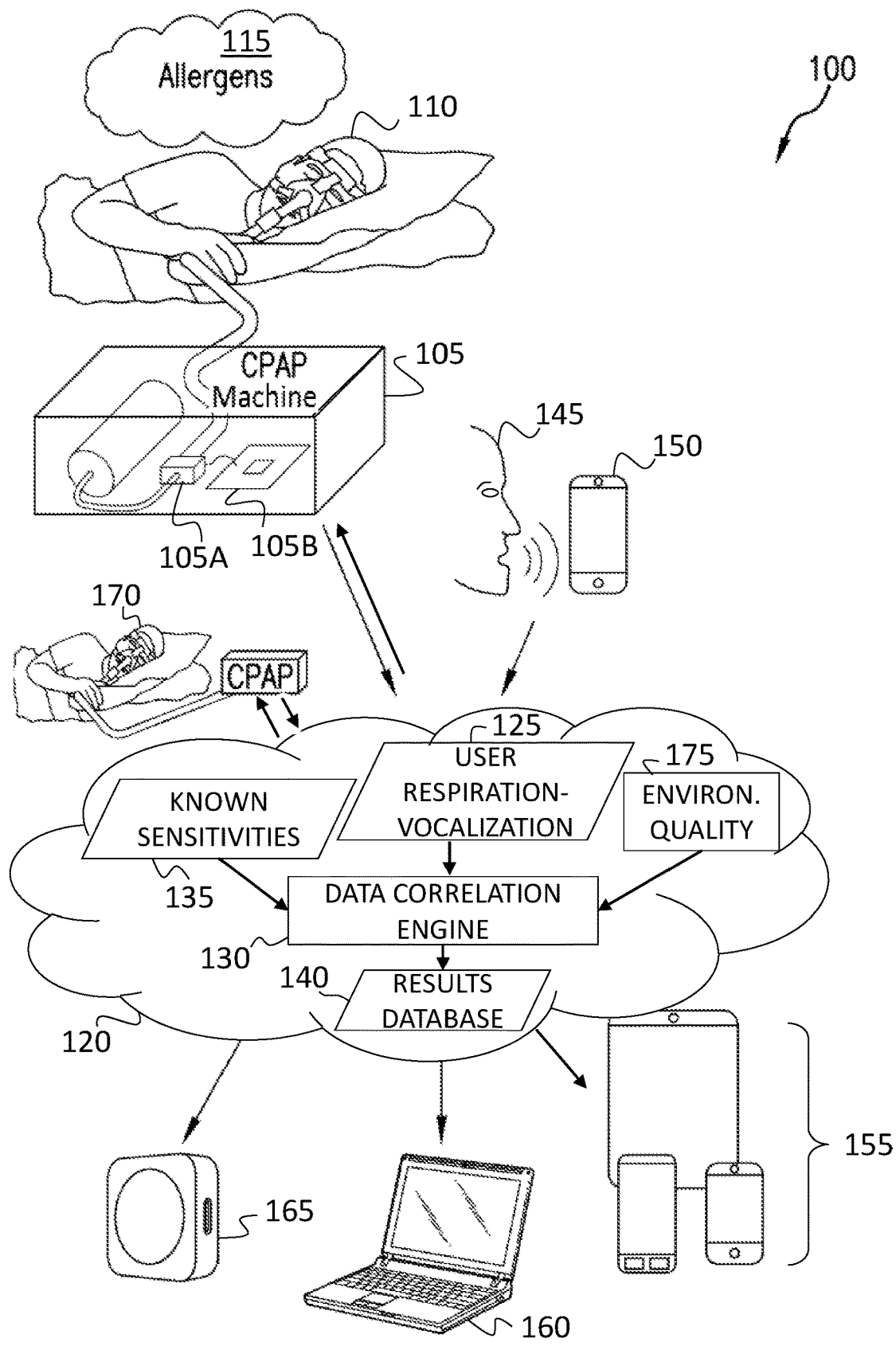
FIG. 1 depicts an exemplary respiration-vocalization data-acquisition system (RVDAS), determining environmental quality information by correlation of user respiration-vocalization data with parameters from users with known sensitivities and/or with regional environmental quality data.
Figure 6:
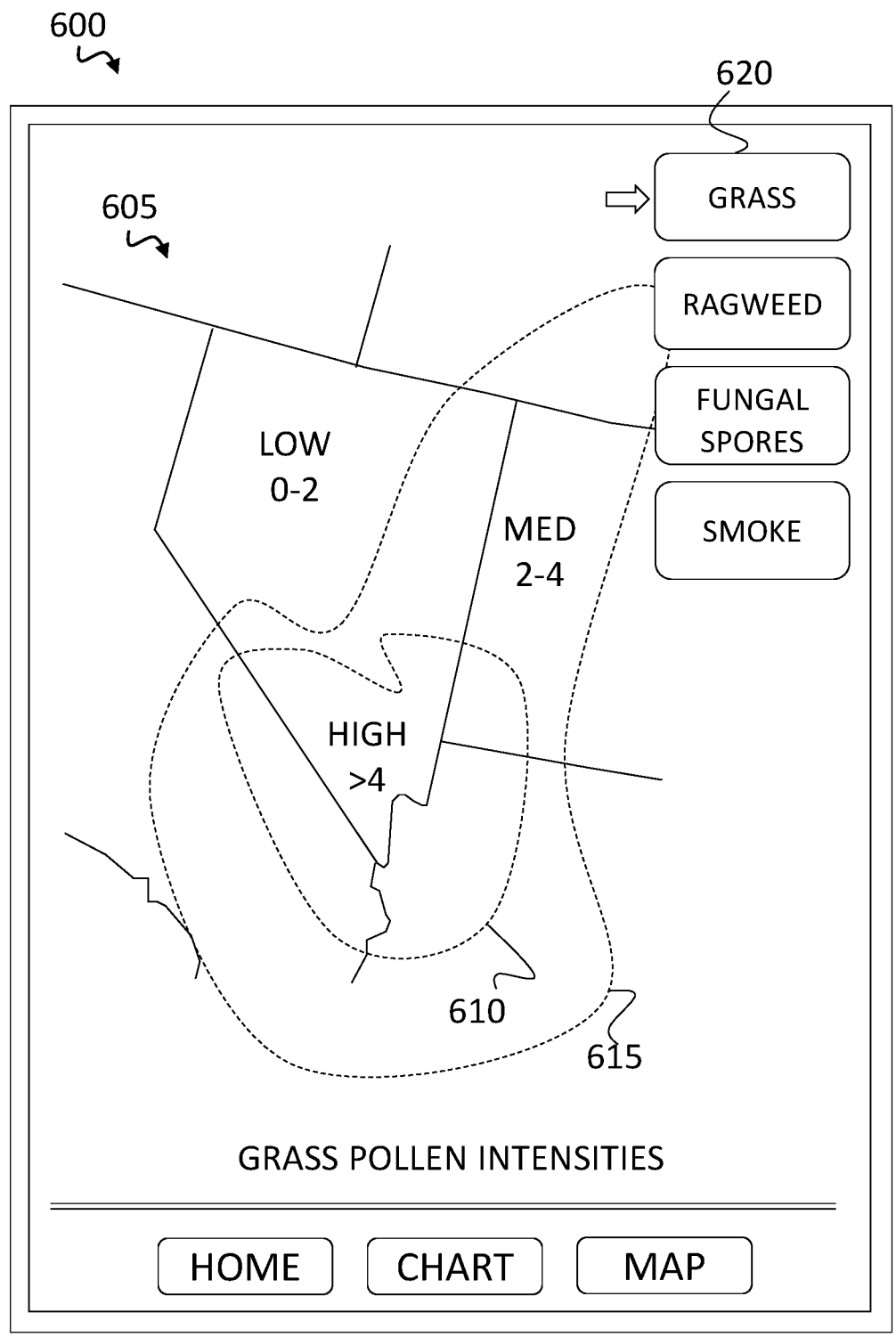
FIG. 6 depicts an irritant map for an exemplary RVDAS.
Figure 7:
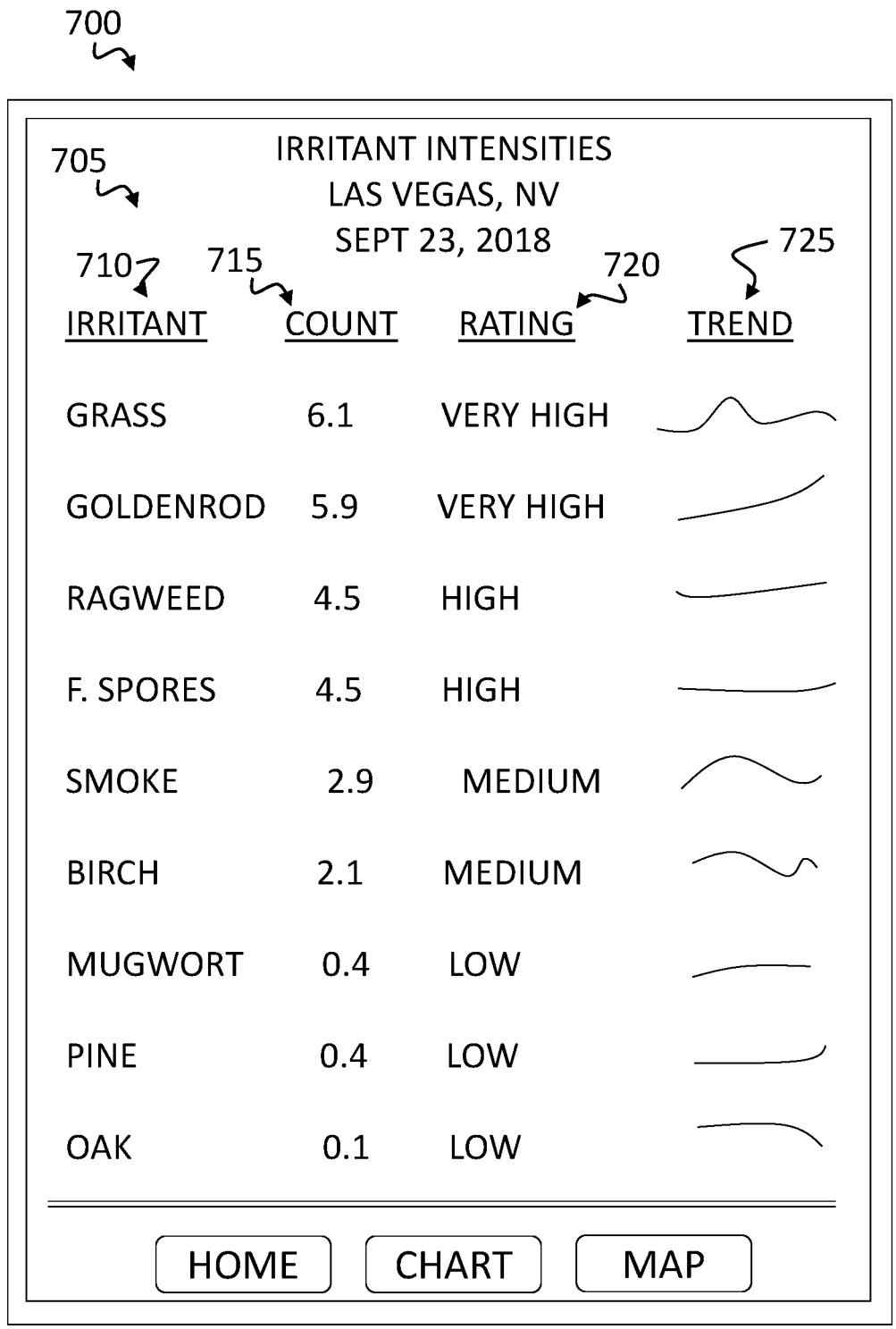
FIG. 7 depicts an irritant chart for an exemplary RVDAS.
Figure 8:
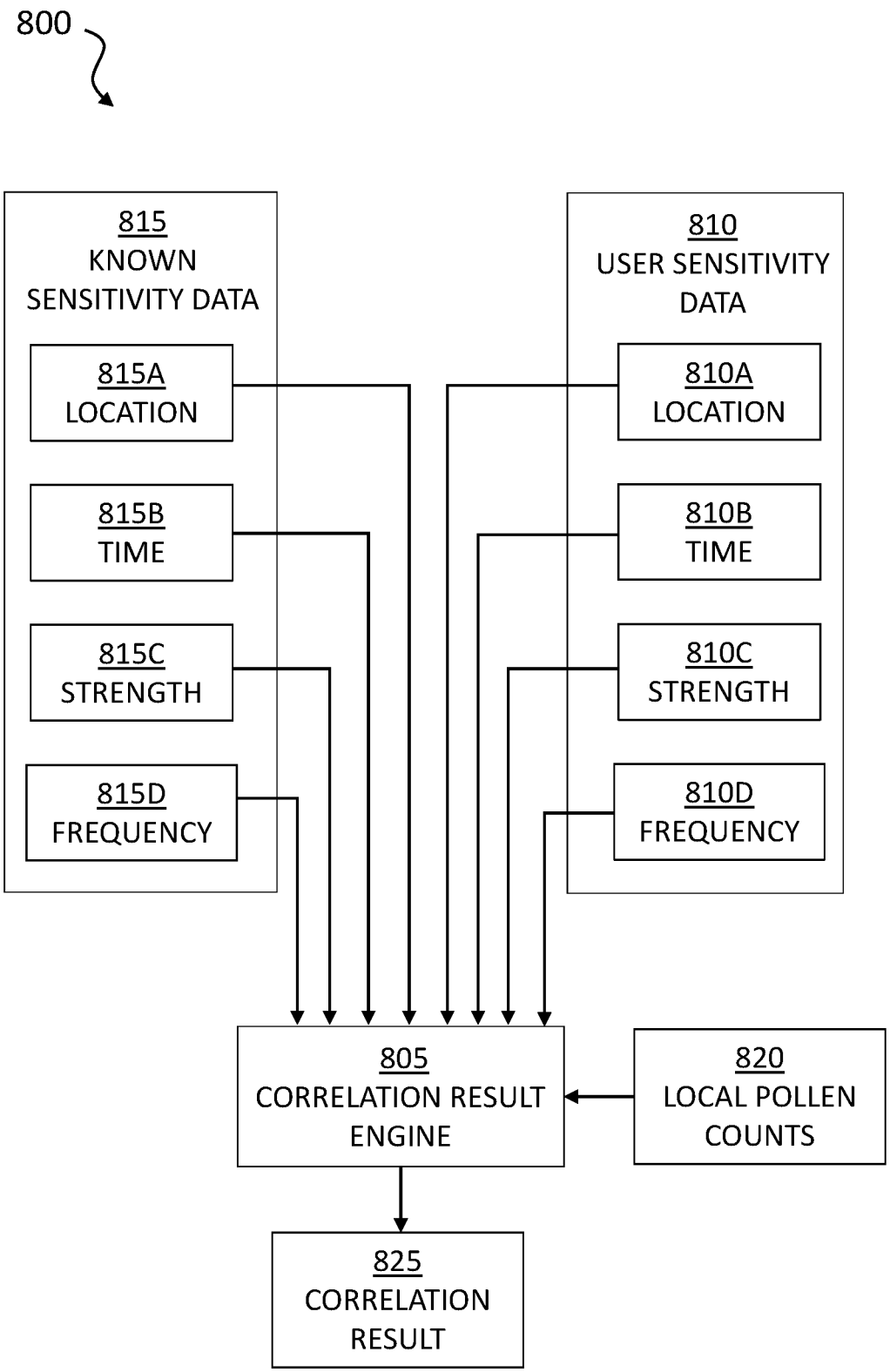
FIG. 8 depicts a diagram illustrating an exemplary method used to determine a correlation result in an RVDAS.

To aid understanding, this document is organized as follows. First, a respiration-vocalization data-acquisition system (RVDAS) for determining local environmental quality RVDAS is presented in FIG. 1, illustrating reception of respiration-vocalization data from a user, correlating the data with regional environmental quality data and/or with respiration-vocalization data from nearby users with known sensitivities, and displaying the results on various devices. Block diagrams of exemplary CPAP and smart phone subsystems are briefly introduced with reference to FIGS. 2 and 3. Next, with reference to FIG. 4, the discussion turns to a flowchart outlining the method in which the server on the cloud network creates the sensitivities databases. Further in FIG. 5, an additional flowchart is presented, outlining an exemplary method in which the server cooperates with the cloud connected devices to produce maps and charts indicating the intensities of various irritants (e.g., allergens, dust, pollutants). FIGS. 6 and 7 present exemplary screen shots from various user devices. Finally, FIG. 8 presents and exemplary data flow diagram outlining how various databases may be used to produce a correlation result, which may be used to determine a user's sensitivities.

FIG. 1 depicts an exemplary respiration-vocalization data-acquisition system (RVDAS), determining environmental quality information by correlation of user respiration-vocalization data with parameters from users with known sensitivities and/or with regional environmental quality data. An exemplary use-case scenario 100 includes a continuous positive airway pressure (CPAP) machine 105. The CPAP machine 105 is coupled to a user 110. As the user 110 sleeps, various allergens 115 may be breathed in. In response to breathing the allergens 115, the user may experience swelling of an airway and therefore may exhibit variations, or disturbance events, in breathing. For example, the user may experience disturbances such as coughing, wheezing, or sneezing. The CPAP machine 105 is operatively coupled to a cloud network 120. By employment of the CPAP machine 105, the user's breathing is monitored by an air sensor 105A. The air sensor 105A is read by a controller 105B and various data is collected and processed. This data may be the respiration-vocalization data and may contain airflow and/or pressure data. The respiration-vocalization data along with location data, is sent from the CPAP machine 105 to a server on the cloud network 120, where a user respiration-vocalization database 125 is constructed. The user respiration-vocalization database 125 is a collection of data from the CPAP machine 105 that is associated with a specific user. The server on the cloud network 120 includes a data correlation engine (DCE) 130 operative to correlate the user respiration-vocalization database 125 with a known sensitivities database 135 from users/patients with known irritant sensitivities and/or with regional environmental quality data 175. The regional environmental quality data 175 may be obtained from the cloud network 120 (e.g., weather website, allergy web resource, Environmental Protection Agency (EPA) maps). The DCE 130 uses the correlation results to construct a results database 140. By way of example, and not limitation, the results database 140 may indicate specific allergens, allergen intensities, and allergen locations. In some embodiments, the DCE 130 may construct an allergen intensity map from the results database 140, the map indicating relative intensities of specific allergens with respect to a geographic region. The air sensor 105A 105B within the RVDAS may measure the user's response to environmental quality. As such, the RVDAS-enabled CPAP may function as an indirect environmental sensor.

In the depicted example, the known sensitivities database 135 is constructed by the server on the cloud network 120 from data associated with users/patients with known irritant sensitivities 170. The RVDAS system accuracy may be dependent upon the data from users/patients with known irritant sensitivities 170. In an illustrative example, when the users/patients with known irritant sensitivities 170 are sending data (e.g., airflow, respiratory disturbance amplitude and/or frequency, pressure, location, time) to the server on the cloud network 120, the server uses that data to construct the known sensitivities database 135. The DCE 130 makes the correlation between the reactionary symptoms of the users/patients with known irritant sensitivities 170 and the user 110, via the known sensitivities database 135 and the user respiration-vocalization database 125, to determine various user-specific allergy sensitivities.

In the depicted example, the RVDAS also includes a user 145 speaking into a smart phone 150. Internal to the smart phone 150, is an application which is operable to receive the microphone signal as the respiration-vocalization data. The application may process the data locally or remotely to detect various shifts in the voice of the user 145. The respiration-vocalization data, along with location data, are sent from the smart phone 150 to a server on the cloud network 120, where the user respiration-vocalization database 125 is constructed. The DCE 130 correlates the user respiration-vocalization database 125 with the known sensitivities database 135 and/or regional environmental quality data 175. Accordingly, the correlation results are used by the DCE 130 to construct the results database 140. The DCE 130 may provide crowd-sourced information about the allergens or illness in an area. The smart phone 150 may measure the user's response to environmental conditions. As such, the smart phone 150 with the RVDAS application may function as an indirect environmental sensor.

Various cloud connected devices may access the results database 140, for example, personal portable electronic devices (PEDs) 155, personal computers 160, and air quality devices (AQDs) 165. In various examples, the CPAP machine 105 and the smart phone 150 may also access the results database 140. The cloud connected devices may display the results database 140 in various formats. For example, the various formats may include an allergen intensities map of a requested region. In some examples, the various formats may include charts of statistical data, such as pollen counts, pollutant counts and/or various environmental agency indicators. In some embodiments, the cloud connected devices may provide various graphical user interfaces (GUIs) to interact with the cloud connected device users. For example, a GUI may present the device user with several buttons or hyperlinks that may be pressed by the device user to select, for example, specific irritants. Once selected, the GUI may present the device user with a geographic map indicating an intensity gradient for the selected irritant. Further, once selected, the GUI may present the device user with a chart containing objective data, for instance, pollen counts.

The DCE 130 processes the data from the CPAP machine 105 and combines it with the known sensitivities database 135 and/or regional environmental quality data 175. Accordingly, the regional environmental quality data 175 may advantageously provide additional data to increase the accuracy or resolution of the databases 125 and 135. In some instances, the regional environmental quality data 175 may fill in missing data due to a substantially low number of users/patients with known irritant sensitivities 170 connected to the cloud network for a given region.

With reference to the smart phone 150 application, detected voice shifts may be a function of various irritants in the air breathed by the user. Accordingly, one or more of the irritants present may cause specific changes in the respiration-vocalization data. The respiration-vocalization data may include voice pitch changes, for example, the pitch of the voice of the user 145 may lower in response to an incipient cold, flu or allergic reaction. In some examples, the voice shifts may include hoarseness in response to air pollutants, illness or allergic reaction. The voice pattern of the user 145 may shift, for example, the user may speak with a slower cadence, or slower inflections which may indicate an incipient or current illness or an allergic reaction.

Figure 2:
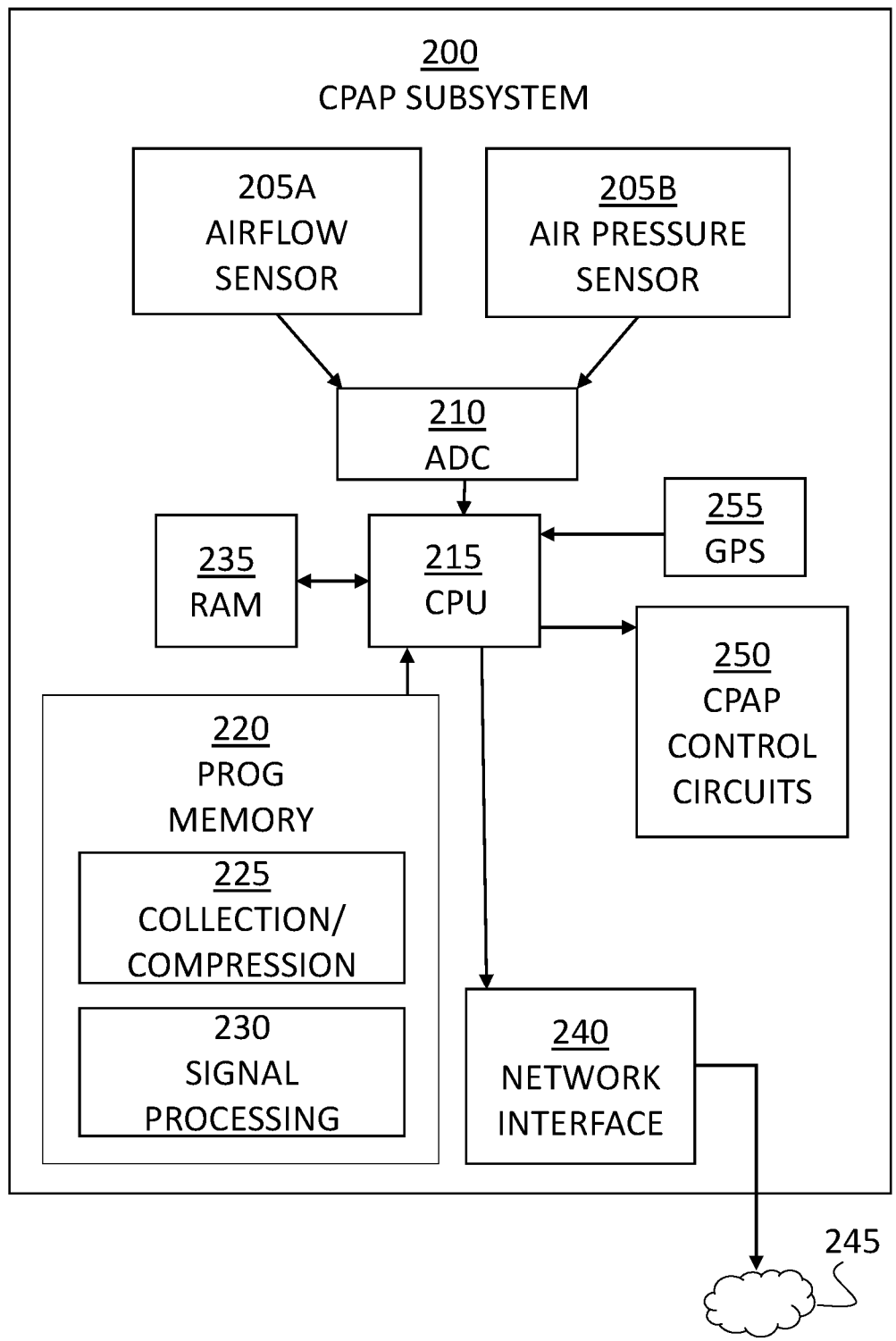
FIG. 2 depicts a block diagram view of an exemplary CPAP subsystem with respiration-vocalization data acquisition and processing to provide local environmental quality data to a central server.

FIG. 2 depicts a block diagram view of an exemplary CPAP subsystem with respiration-vocalization data acquisition and processing to provide local environmental quality data to a central server. A CPAP subsystem 200 includes an airflow sensor 205A and an air pressure sensor 205B. The airflow sensor 205A and the air pressure sensor 205B are operatively coupled to an analog to digital converter (ADC) 210. The ADC 210 is operable to convert the signal from the airflow sensor 205A and the signal from the air pressure signal 205B to digital numeric data values. The ADC 210 is operably coupled to a CPU 215. The CPU 215 receives user-specific airflow and air pressure digital numeric data values from a user via the airflow sensor 205A and the air pressure sensor 205B via the ADC 210. The CPU 215 executes pre-programmed instructions from a program memory 220. The CPU 215 collects and compresses the digital numeric data values from the ADC 210 via a pre-programmed collection/compression module 225 within the program memory 225. The CPU 215 processes the digital numeric data values in a preprogrammed signal processing module 230 to produce various trending parameters. The preprogrammed signal processing module 230 may employ various filters (e.g., Fast Fourier Transform (FFT)) to aid in producing the trending parameters. The CPU 215 saves the respiration-vocalization data in a random-access memory (RAM) 235. The CPU 215 is operably coupled to a network interface 240. The network interface 240 operably couples to an external network 245, for example, the Internet. The respiration-vocalization data are sent to the external network 245 via the network interface 240. For completeness, the CPU 215 is also depicted controlling a CPAP control circuit 250. The CPAP circuit may, for example, control various valves, read switch inputs from the user, control audible alarms, and turn on various visual indicators. In some examples, a microcontroller may include the CPU 215, the program memory 220 the RAM 235 and the ADC 210.

The airflow sensor 205A and the air pressure sensor 205B may be pneumatically coupled to a user. The user may have known airborne irritant reactions to specific airborne particles. The airflow sensor 205A and the air pressure sensor 205B may sense the user's airborne irritant reactions based on shifts in the user's baseline airflow and/or air pressure readings. The CPU 215 may process airflow and air pressure data originating from the airflow sensor 205A and the air pressure sensor 205B, and send various respiration-vocalization data to a network server. The CPU 215 may also send location data that may be statically programmed on the CPAP subsystem 200. In some examples, the location data may be automatically determined, for example, via an internet-connected modem, wireless network, or global positioning sensor (GPS) 255 onboard the CPAP subsystem 200. The respiration-vocalization data may aid various environmental groups (e.g., allergen resource groups, Environmental Protection Agency (EPA), environmental product manufacturers) in determination of the presence of specific particles in specific geographic locations. Further, multiple users with a variety of known airborne irritant reactions to known airborne particles may send data to the network server. Accordingly, the accuracy and resolution of the RVDAS may be improved as the number of users with known airborne irritant reactions increases.

Figure 3:
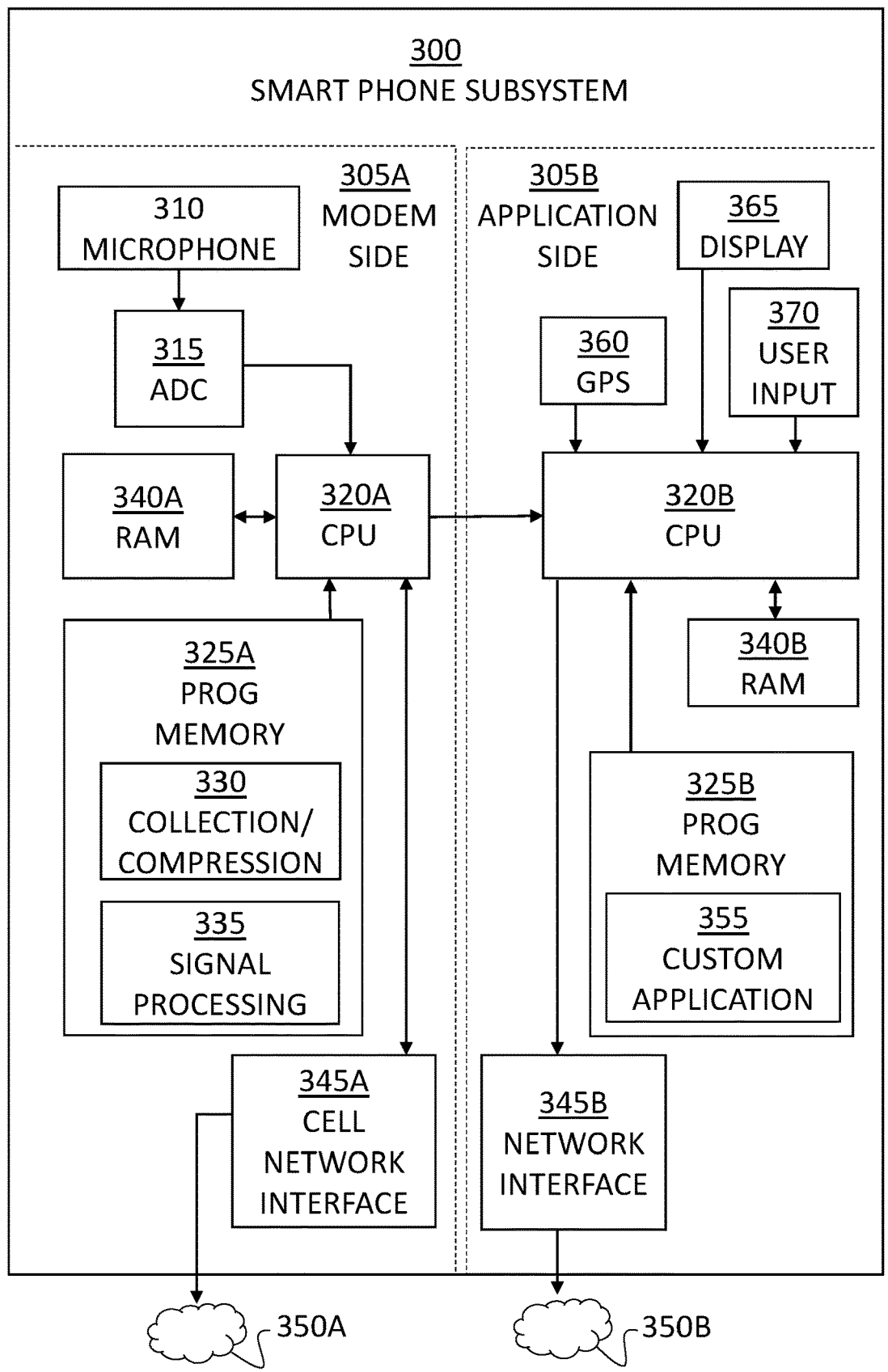
FIG. 3 depicts a block diagram view of an exemplary smart phone subsystem with respiration-vocalization data acquisition and processing and functionality to accept known sensitivity inputs from the user to provide local environmental quality data sensitivity trending parameters to a central server.

FIG. 3 depicts a block diagram view of an exemplary smart phone subsystem with respiration-vocalization data acquisition and processing and functionality to accept known sensitivity inputs from the user to provide local environmental quality data sensitivity trending parameters to a central server. A smart phone subsystem 300 includes a modem side 305A and an application side 305B. The modem side 305A includes a microphone 310. The microphone 310 is operably coupled to an ADC 315. The ADC 315 is operable to convert the signal from the microphone 310 to digital numeric data values. The ADC 315 is operably coupled to a CPU 320A. The digital numeric values from the ADC 315 are sent to the CPU 320A. The CPU 320A executes pre-programmed instructions from a program memory 325A. The CPU 320A collects and compresses the digital numeric data values from the ADC 315 via a pre-programmed collection/compression module 330 within the program memory 325A. The CPU 320A processes the digital numeric data values in a preprogrammed signal processing module 335 to produce various trending parameters. The trending parameters may represent, for example, a quality, or change in quality, of a respiratory vocalization state, such as the human voice. The preprogrammed signal processing module 230 may employ various filters (e.g., Fast Fourier Transform (FFT)) to aid in producing the trending parameters. Frequency selective filtering may be applied to, for example, analyze the frequency content of the voice in selected frequency bands. The CPU 320A saves the trending parameters in a random-access memory (RAM) 340A. The CPU 320A is operably coupled to a cellular network interface 345A. The cellular network interface 345A operably couples to an external cellular network 350A. The trending parameters are sent to the external cellular network 350A via the cellular network interface 345A. In some examples, a microcontroller may include the CPU 320A, the program memory 325A the RAM 340A and the ADC 315.

In some embodiments, the trending parameters may be transported to the application side 305B where they are received by a CPU 320B on the application side. The CPU 320B executes pre-programmed instructions from a program memory 325B, and employs a RAM 340B for basic operation. The CPU 320B is operably coupled to a network interface 345B. The network interface 345B operably couples to an external network 350B. The trending parameters are sent to the external network 350B via the network interface 345B.

In some examples, the voice data from the ADC 315 may be transported directly to the application side 305B (without being processed by the preprogrammed collection/compression module 330, and the preprogrammed signal processing module 335). In such examples, the voice data may be processed by the CPU 320B by execution of a preprogrammed custom application (app) 355 within the program memory 325B on the application side 305B. The process results may be substantially similar to the trending data on the modem side 305A output from the preprogrammed signal processing module 335.

The CPU 320B is operably coupled to a GPS 360. The GPS 360 may provide the CPU 320B location information along with the trending data, to provide the network server information for the results database (FIG. 1, item 140). The CPU 320B is also operably coupled to a display 365 and a user input 370. The display 365 and the user input 370 allow the operator to interact with the custom application 355. In various examples, a microcontroller may include the CPU 320B, the program memory 325B, the RAM 340B and the ADC 315.

The user's voice is received by the microphone 310. The user may have known respiratory reactions to known airborne substances. The microphone 310 may sense the user's respiratory reactions based on shifts in the user's baseline voice level and/or patterns. The CPU 320B may process voice data originating from the microphone 310, and send various trending data to a network server. The CPU 320B may also send location data that may be manually programmed on the smart phone subsystem 300. In some examples, the location data may be automatically determined via the GPS 360 onboard the smart phone subsystem 300.

Figure 4:
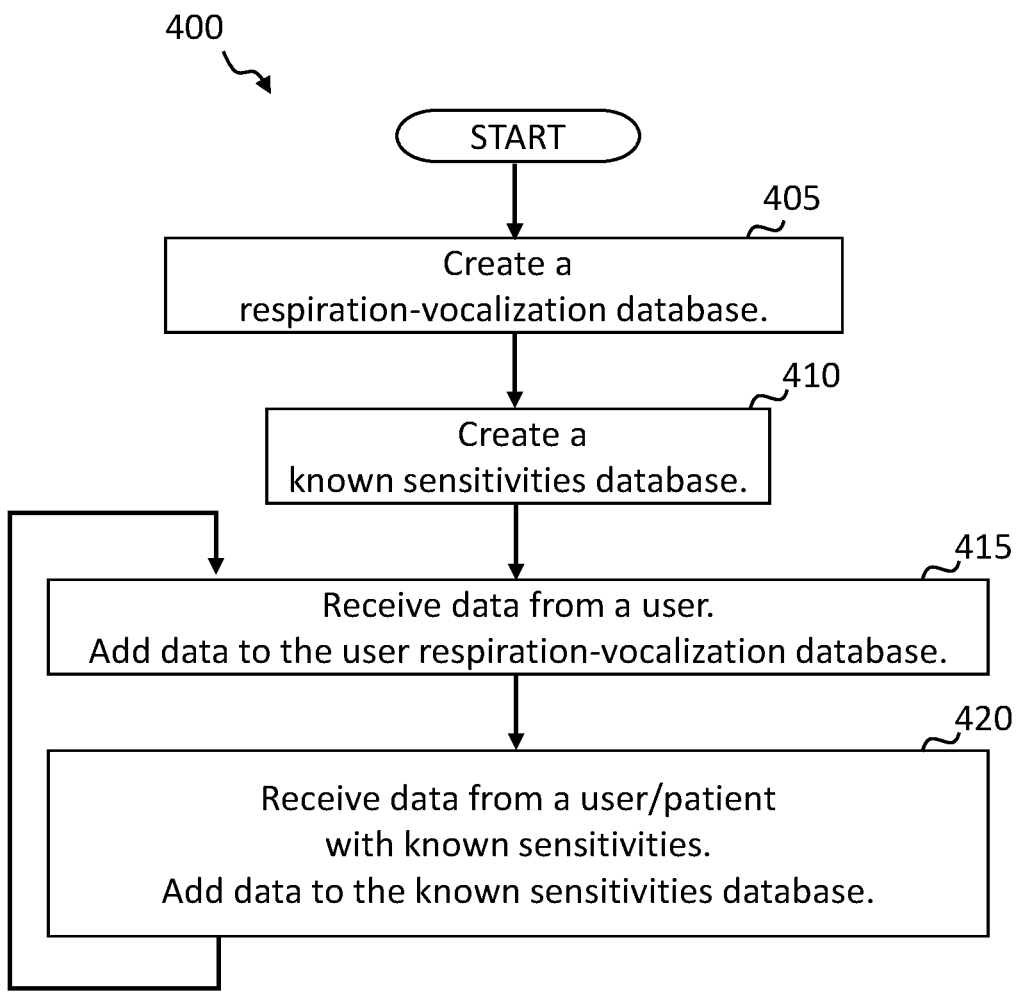
FIG. 4 depicts a flowchart illustrating exemplary method of cloud database creation in an RVDAS.

FIG. 4 depicts a flowchart illustrating exemplary method of cloud database creation in an RVDAS. An exemplary databases creation subroutine 400 includes block 405, where a respiration-vocalization database is created at the cloud server. Next, at block 410 a known sensitivities database is created at the cloud server. Next at block 415, data is received from a user, and appended to the user sensitivities database. Data may include airflow and/or pressure readings from a CPAP machine, paired with time of day and/or location. Next, block 420 is executed, where data is received from a user/patient with known irritant sensitivities, and the known sensitivities database is appended. Again, data may include airflow and/or pressure readings from a CPAP machine, paired with time of day and/or location. Next, the exemplary databases creation subroutine 400 continues in a loop, gathering data and adding to the databases. As more and more data is gathered by the RVDAS, the system may produce sensitivity correlation results with higher degrees of confidence. This higher confidence may advantageously produce, for example, a higher degree of certainty from the RVDAS that a particular user has a specifically identified particle sensitivity.

In some implementations, the known sensitivities database may be used as a calibrated detector or an indicator to the system of the presence of specific irritants in the location of a population of users. User sensitivities from the respiration-vocalization database may be compared with known sensitivities to determine time correlations of user and known activities. Sensitivities that correlate in time between the user and the known sensitivities databases may indicate a user sensitivity to the irritant from the known sensitivities database. In an illustrative example, if a user/patient with known irritant sensitivities shows sensitivity starting at 2:00 AM as indicated by the associated known sensitivities database, and a user shows sensitivity starting at 2:00 AM as indicated by the associated user sensitivity database, there is high correlation and therefore a high likelihood that the user shares a common irritant with the user/patient with known irritant sensitivities.

Figure 5:
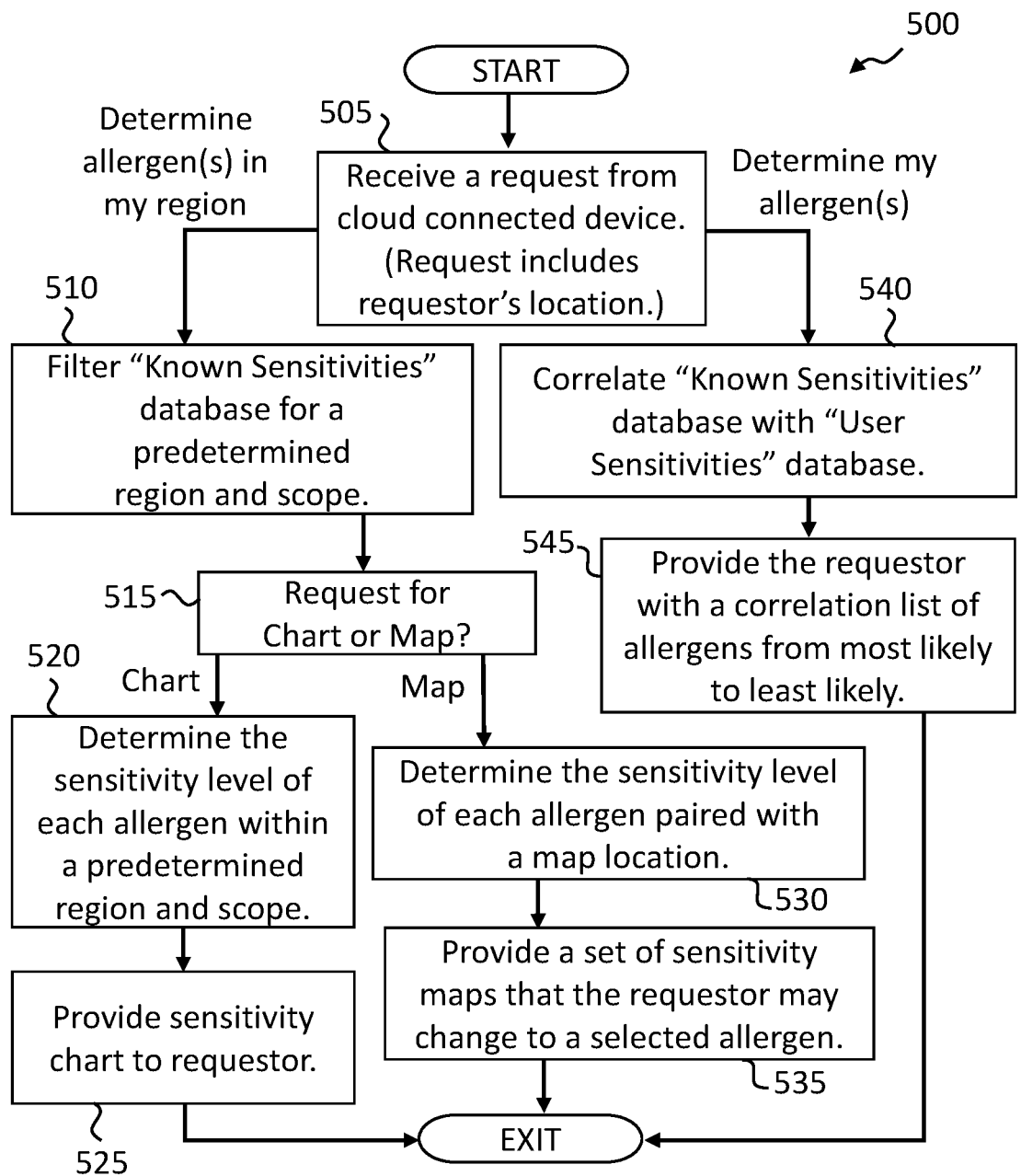
FIG. 5 depicts a flowchart illustrating exemplary method of cloud connected device queries of a results database in an RVDAS.

FIG. 5 depicts a flowchart illustrating exemplary method of cloud connected device queries of a results database in an RVDAS. An exemplary cloud connected request subroutine 500 includes block 505, where the RVDAS receives a request from a cloud connected device. The request includes the requester's location.

If the request from the cloud connected device was to determine allergens in the requester's region, then execution flows to block 510, where the subroutine filters the known sensitivities database for a predetermined region and scope. Next, in block 515, the subroutine determines if the requester has requested a chart or a map.

If the requester has requested a chart, then in block 520 the subroutine determines the sensitivity level of each allergen within a predetermined region and scope. Next, in block 525 the sensitivity chart is provided to the requester and the subroutine is exited.

If the requester has requested a map, then in block 530 the subroutine determines the sensitivity level of each allergen paired with a geographic map location. Next, in block 535 a set of sensitivity maps is provided to the cloud connected device. The requester may be provided selection buttons to change the display to a selected allergen. In some examples, the requester may be allowed to select more than one allergen, thereby overlapping allergen regions. The subroutine is then exited.

Returning to block 505, if the request from the cloud connected device was to determine the requester's allergen(s), then execution flows to block 540, where the subroutine correlates the known sensitivities database with the user sensitivities database. Next, in block 545, a correlation list of allergens is provided to the requester. In some embodiments, the list may be sorted from allergens that are most likely, to allergens that are least likely to be causing the users symptoms. The subroutine is then exited.

FIG. 6 depicts an irritant map for an exemplary RVDAS. An irritant map includes a display screen 600. The display screen 600 shows a map of a geographic region 605. The map of the geographic region 605 is superimposed with a high-to-medium irritant intensity contour 610 and a medium-to-low irritant intensity contour 615. In the depicted example, the contour delineates between three different concentrations: high, medium, and low. The user may select the type of irritant from a list of irritant selection buttons 620. In the depicted example, the user has selected grass pollen intensities. The user may advantageously view intensity maps for a selected region and a selected type of irritant to determine the intensities present.

FIG. 7 depicts an irritant chart for an exemplary RVDAS. An irritant chart includes a display screen 700. The display screen 700 shows an irritant chart 705 of a selected location. The irritant chart 705 includes a list of irritants 710 which are present in the location. The irritant chart 705 also includes an irritant particle count 715. The particle counts 715 may advantageously provide the user with an objective irritant level of each irritant in the selected location. The irritant chart 705 also includes a rating of each irritant 720, indicative of the comparative level of the irritant (e.g., high, medium, low). In various examples, the rating of the irritant 720 may be portrayed as a color (e.g., red, yellow, green). Finally, as depicted, the irritant chart 705 includes a trending line 725. The trending line 725 may advantageously help the user predict future intensities or help personally correlate historical symptoms with the irritant. In some embodiments, other parameters may be included.

FIG. 8 depicts a diagram illustrating an exemplary method used to determine a correlation result in an RVDAS. A correlation method 800 includes a correlation result engine 805. The correlation result engine 805 receives user sensitivity data 810. The user sensitivity data 810 may be collected from network connected devices (e.g., smart phone, CPAP). The correlation result engine 805 also receives known sensitivity data 815. The known sensitivity data 815 may be collected from network connected devices. The user sensitivity data 810 is populated with general user data. The known sensitivity data 815 is populated with data from users/patients with known allergen sensitivities. Finally, the correlation result engine 805 receives a local pollen count 820. The correlation result engine 805 is operable to determine allergens present in the air, outputting a correlation result 825 in response to the depicted inputs.

The user sensitivity data 810 includes a location property 810A. The known sensitivity data 815 also includes a location property 815A. The correlation result engine 805 may provide a higher confidence on the correlation result 825 for the location properties 810A and 815A in close proximity. For those location properties 810A and 815A that are further away from each other, the lower the confidence on the correlation result 825.

The user sensitivity data 810 includes a time property 810B. The known sensitivity data 815 also includes a time property 815B. The correlation result engine 805 may provide a higher confidence on the correlation result 825 for the time properties 810B and 815B coincident in time.

The user sensitivity data 810 includes a strength property 810C. The known sensitivity data 815 also includes a strength property 815C. The strength properties 810C and 815C may correspond to amplitude of the user's voice change (e.g., hoarseness) or cough. The correlation result engine 805 may provide a higher confidence on the correlation result 825 when either of the strength properties 810C and 815C are higher.

The user sensitivity data 810 includes a frequency property 810D. The known sensitivity data 815 also includes a frequency property 815D. The frequency properties 810D and 815D may correspond to the number of user coughs per unit time. The correlation result engine 805 may provide a higher confidence on the correlation result 825 when either of the frequency properties 810D and 815D are higher.

The correlation result engine 805 receives the local pollen count 820. The local pollen count 820 may be acquired from an online source (e.g., National Weather Service). The local pollen count 820 data may be combined with the user sensitivity data 810, and the known sensitivity data 815 to help make correlations and or to increase accuracy of the correlation result engine 805.

The correlation result engine 805 may execute continuously, updating the correlation result 825 continuously. In some embodiments, the correlation result engine 805 may execute at a predetermined update interval. For example, the update interval may be about once a second, once a minute, three times a minute, six times a minute, once an hour, three times an hour, six times an hour, or about once a day. In some implementations, the updates may be aperiodic, such as on an as available basis, to conserve bandwidth by not reporting null data when the user respiratory vocalization state has not been measured.

As more users with known sensitivities add data to the system database, the more accurate the system becomes at identifying specific allergens for specific users, and the more confidence can be placed on the results. Further, as more accurate and higher resolution airflow and pressure sensors are employed, various irritants causing similar symptoms may be differentiated, which may allow proper and more effective medications or therapy to be prescribed.

Although various embodiments have been described with reference to the figures, other embodiments are possible. For example, some embodiments may automatically adjust the environmental controls at the user's home, in response to the trending parameters. For example, the RVDAS may turn on air-conditioning or adjust humidity levels. This feature may advantageously provide a level of freedom for the user. The user may a find a degree of relief by not having to worry about monitoring his symptoms or about adjusting environmental settings.

In some embodiments, the known sensitivities database may be collecting real-time data, similar to the user sensitivities database to facilitate the determination of when the user is reacting co-incident with the known sensitivities user, thus may be an indicator that the user has the same allergies as the known user/patient. In some examples, the known sensitivities database may be a static database that shows how the known user/patient reacts to certain irritants. Accordingly, in such examples, a user's data may correlate to the known user/patient's data, regardless of time or location.

Various smart phone embodiments may provide one or more Application Programming Interfaces (APIs) to application developers. The APIs may operably couple the speech processing section of the smart phone (e.g., the modem side, FIG. 3, item 305A) to the application processor (e.g., the CPU, FIG. 3, item 320B). The APIs may provide information about, for example, coughs and/or hoarseness, in addition to user voice characteristics (e.g., tone, frequency, pitch, cadence). Further, various applications (apps) may prompt users about their allergies and may inquire about the user's health when voice changes are detected.

In some examples, data analysis (analytics) in a network server may weigh the inputs from various users differently, depending on the level of the user's specific irritants. Further, the severity of the user's reaction to the irritants may be entered into the data analysis based on results from standardized allergy testing.

In an illustrative example, data analysis in a network server may create a pollen allergy map based on the data collected from the various users with known allergies. The data analysis may be augmented with known local allergy concentrations from pollen count stations across the country. The known local allergy concentrations may be automatically acquired via the cloud network. The RVDAS may augment physical sensors with cloud based data for increased performance.

In some examples, various indexes, such as $PM_{2.5}$, which indicates the number of micrograms of particles less than 2.5 μm within a cubic meter of air, may be advantageously supplemented or improved by the RVDAS, since the RVDAS may indicate what specific allergens or other irritants are in the air in specific locations. Further, the RVDAS may employ big data analytics. For example, big data analytics may take in the cell phone voice parameters, the CPAP air parameters, and local irritant counts, to advantageously produce an accurate map of allergen intensities and locations. Further, the RVDAS may perform various analytics on the databases constructed.

In some embodiments, the results database may be displayed in various forms on a website. For example, a RVDAS website may provide an allergen intensities map of a requested region. The website may provide charts of statistical data, such as pollen counts, pollutant counts and/or various environmental agency indicators (e.g., $PM_{2.5}$). The website may provide various resource guides. For instance, the website may provide links to various web resources, or may provide site-local information regarding allergens, pollutants, environmental trends, and/or news articles regarding air quality. Further, the website may provide historical data, outlining, for instance, what the various particle counts were yesterday, or a year ago.

In various embodiments, the results database may be accessed by various cloud connected devices. The server on the cloud network may determine intensities of allergens and airborne pollutants in relationship to geographic location from the results database. The intensities and locations may be transmitted and mapped on various cloud connected devices. This mapping may be referred to as a "heatmap" and may show sensitivity trends over an area. Various statistics may be generated, advantageously providing the user with a detailed report of allergens and other irritants in the user's specific area. In an illustrative example, the CPAP machine may be connected to the cloud network. The connection may not only facilitate provision of the user's sensitivity trending data, but may also facilitate gathering data from the server to generate various intensity maps and charts. These features resident on the CPAP machine may provide the user a convenient single point of airborne sensitivities resources.

Further, other respiratory sensitivities of non-typical allergens, for example, various forms of air pollution (e.g., dirt, soot, smoke, smog, airborne chemicals) may be detected within the RVDAS in the same manner as allergens. In an illustrative example, a user/patient with known irritant sensitivities may have a sensitivity to smoke. A CPAP user may exhibit correlation between the user/patient with known irritant sensitivities having a sensitivity to smoke, thereby determining that the user likely has a smoke sensitivity.

In various examples, certain illnesses (e.g., common cold, latest flu) may be detected. For example, certain airflow and/or pressure profiles may be determined to be a characteristic of a seasonal cold. In various examples, certain spacing between coughs or sniffles may be indicative of the flu.

In various examples, the RVDAS may be advantageously employed to aid users in diagnosing allergen sensitivities. As the number of user/patient with known irritant sensitivities included in the RVDAS increases, the accuracy and resolution of the RVDAS increases as well. As the sensitivity of the airflow sensor and or the pressure sensor within the CPAP increases, the distinction between various user reactions may become greater. This increased user reaction distinction may advantageously increase the number of possible irritants that may be detected, and may provide users with a severity level of their allergies. Knowing the severity level of a user's allergies may allow doctors to prescribe medication dosages more accurately. In some instances, the severity level of the user's allergies may allow doctors to prescribe more appropriate types of medication or therapies.

The information provided within the databases may provide various advantages. Therefore, it is contemplated that those in possession of the databases may sell, rent or provide access to the databases in an effort to provide their customers the ability to discover their own specific respiratory sensitivities.

In various smart phone embodiments, the RVDAS may establish a baseline from a voice. The phone may then periodically sample the voice within the phone via an application in combination with modem-resident firmware to determine when the voice shift is over a threshold, triggering an indicator. The indicator may alert the phone user of an impending illness, for example, an impending cold. The user may then take action, such as drinking more water or getting more sleep. In some examples, the indicator may alert the phone user of the presence of an allergen. Again, the user may take action, such as taking an antihistamine, or increasing indoor humidity. In some examples, the indicator may not only alert the user but may suggest various actions for the user to take, for example, to increase humidity in the house or to medicate. Accordingly, if the user reacts promptly, the symptoms may be immediately treated. Such immediate action may advantageously avoid worsening health conditions, for instance, developing a cough from post nasal drip.

In some examples, with reference to smart phone embodiments, the smart phone may be monitoring the user's voice both when on a phone call and when not on a call. The continuous voice monitoring may provide the airborne sensitivity functions regardless of the frequency of use of the phone conversation function.

In various air-quality device examples, the devices may connect to a cloud network to access the various RVDAS databases. With the information from the RVDAS databases the air-quality devices may display allergen and/or pollution information along with temperature and humidity information. Providing the allergen and/or pollution information on the air-quality device may advantageously provide a convenient place for users to look for environmental parameters.

In some implementations, the RVDAS may employ various statistical techniques to determine a statistical relationship value between the at least one record and each of one or more known sensitivities records stored in the data storage system. The statistical relationship value could be the result of a polynomial function. The function may combine various inputs with weightings for those inputs. For example, the ragweed pollen count using a "sticky rod" from local pollen counts, may be one term in the polynomial with a corresponding weighting. The aggregate of all data from users with known sensitivities may be another term in the polynomial.

The statistical relationship value could be derived by employment of various types of statistical measures (e.g., confidence interval, rank, Pearson correlation, robust statistic). The Pearson or product-moment correlation may be the most common type of statistical relationship value, and may therefore give a good general result, working best with linear relationships. A variation of the product-moment correlation is the partial correlation. The partial correlation may be a useful statistical relationship value when comparing relationships between two variables. Rating scales may be employed to find statistical relationship values between the records discussed, and may provide general indications. The main result of statistical relationship values may, in some embodiments, be referred to as a correlation coefficient, for example.

In some examples, the CPAP machine may be referred to as a local device, and may be configured to receive vocalization-respiration data from a user. Various implementations may have access to available environmental quality data that is published for areas around the user. Some embodiments may include a module to correlate changes in the vocalization-respiration data with the published environmental data to produce a measurement of the local environmental quality that has caused the vocalization-respiration data change.

Various examples may be further configured to accept user entered allergy information or other medical information. This information may be regional air quality data, which may be published by a city. In some examples, the information may include a regional database of other users' allergy information and their vocalization-respiration data for normal and for allergic response (e.g., the "known sensitivities database"). Various embodiments may further correlate the local vocalization-respiration with the more regional information that is also available.

In some embodiments, the term "environmental quality" may refer to the probability of contagious diseases. The "known sensitivities database" in this embodiment may include information about how many local people are reacting (e.g., coughing, sneezing, wheezing). Various embodiments may provide early insight to allergen or disease outbreaks.

In an exemplary aspect, a computer program product (CPP) may be tangibly embodied in a computer readable medium and may contain instructions that, when executed, cause a processor to perform operations to determine various user-specific irritant sensitivities. The operations may include (1) receiving data containing respiration-vocalization state information associated with a local monitoring device of a user (2) in response, storing, in a data storage system, at least one record corresponding to the data containing respiration-vocalization state information associated with the local monitoring device of the user (3) accessing environmental quality data pertaining to a predetermined location in proximity to the user (4) determining at least one statistical relationship value representative of a statistical relationship between the at least one record and the environmental quality data, and (5) storing, in the data storage system, the determined at least one statistical relationship value in association with the at least one record.

The respiration-vocalization state information may include voice quality information associated with a sample of the user's speech input to a microphone. The local monitoring device of the user may include a telecommunication device configured to analyze the samples of the user's speech input from the microphone to generate the voice quality information. The respiration-vocalization state information may include respiratory quality information associated with a sample of the user's aspiration input to a sensor. The sensor may be configured to be in fluid communication with the user's respiratory system while the user is wearing a continuous positive airway pressure (CPAP) mask operably coupled to the local monitoring device of the user. The sensor may be an air pressure sensor. The sensor may be an air flow sensor.

The respiratory quality information may include a frequency and an amplitude of one or more respiratory disturbance events during a selected time period. The respiratory quality information may include a spectral content of one or more respiratory disturbance events during a selected time period.

The environmental quality data may include published regional air quality data. The data may be published by a government agency. The environmental quality data may include known sensitivities data, which may include allergy information from other users. The environmental quality data may include known sensitivities data, which may include vocalization-respiration state information for normal and for allergic responses from other users. The at least one statistical relationship value may include a correlation coefficient.

The CPP may include the operation of sending, for display on a display device, the at least one statistical relationship value. The CPP may include the operation of iteratively updating the at least one statistical relationship value upon receiving additional data containing respiration-vocalization state information associated with the local monitoring device of the user.

In some implementations, various output devices may be used to present statistical relationships and/or a predetermined alarm limit. The predetermined alarm limit may correspond to the user's level of sensitivity to one or more airborne irritants (e.g., tree pollen, smoke). Accordingly, the system may advantageously alert users to one or more environmental conditions. The user may then take appropriate countermeasures to mitigate an allergic response (e.g., take medications, move indoors).

The output devices may present text and/or various graphics on a visual display, for example, with reference to FIG. 7, the display may provide the user a list of various allergens and/or other irritants. The list may present to the user a numerical count and/or a graphic indication of what direction the count is headed. In some implementations, the graphic may be a historical trend of the counts. Further, the display may indicate to a user that a predetermined statistical relationship has crossed a predetermined alarm threshold. The indication may be colored and/or flashing icons, colored and/or flashing text or colored and/or flashing backgrounds. The display may present the user with instructions such as "contact your physician" or "best to stay indoors today." With reference to FIG. 6, the user may be presented maps with color coding indicating the severity of the irritant counts, or may be color coded based on nearness to a predetermined or programmed count threshold.

In some embodiments, the output devices may produce an audible output, for example, information in a user's language. The audible output may contain messages such as "contact your physician" or "best to stay indoors today." In some examples, the audible message may indicate the irritant count level along with the predetermined threshold. The audible message may be in natural language, such as "The ragweed count today is 17 and increasing. This count is nearing your threshold of 18." In some implementations, the audible output may be tones or other sounds to indicate alerts, for example. The type of tone may be user-programmable such that the user can distinguish allergy alerts from other alerts such as text messages or phone calls.

In an illustrative example, the output devices may provide haptic feedback and may indicate to a user that the RVDAS has determined that a selected parameter, such as ragweed pollen count, has exceeded a predetermined alarm limit in the user's local environment. The haptic feedback may include vibrations which may be in a specific pattern. The vibration patterns may be user-programmable.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments may be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from a source to a receiver over a dedicated physical link (e.g., fiber optic link, infrared link, ultrasonic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, FireWire, ATA/IDE, RS-232, RS-422, RS-485, 802.11 a/b/g/n, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various embodiments, a computer system may include non-transitory memory. The memory may be connected to the one or more processors may be configured for encoding data and computer readable instructions, including processor executable program instructions. The data and computer readable instructions may be accessible to the one or more processors. The processor executable program instructions, when executed by the one or more processors, may cause the one or more processors to perform various operations.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices. IOT devices may be connected securely to a cloud network via wired or wireless connection.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A non-transitory computer program product tangibly embodied in a computer readable medium and containing instructions that, when executed, cause a processor to perform operations to determine various user-specific irritant sensitivities, the operations comprising:
    receiving data comprising respiration-vocalization state information and a first location property associated with a local monitoring device of a user;
    in response to receiving the data, storing, in a data storage system, at least one record corresponding to the data;
    accessing environmental quality data pertaining to a predetermined location in proximity to the user;

accessing known sensitivities data comprising information associated with other users with known irritant sensitivities and a second location property;

determining at least one statistical relationship value representative of a statistical relationship between the at least one record, the environmental quality data, and the known sensitivities data based on the first location property, the predetermined location, and the second location property via a data correlation engine, wherein the at least one statistical relationship value is associated with a confidence indication that is based at least in part on a proximity level associated with the first location property and the second location property;

storing, in the data storage system, the at least one statistical relationship value in association with the at least one record;

sending, for output on an output device, the at least one statistical relationship value;

wherein the respiration-vocalization state information comprises voice quality information associated with a sample of speech input of the user received at a microphone of the local monitoring device to create baseline data of the user's voice;

automatically activating a respiration-vocalization data acquisition system whenever the user employs his voice to interact with the local monitoring device;

periodically sampling the speech input in order to determine a shift in the voice quality above a threshold level; and triggering an indicator, based on the determination that the shift in the voice quality is above the threshold level and based on the stored baseline data of the user's voice, wherein the baseline data includes at least one of tone, frequency and shift of the user's voice, wherein the indicator alerts the local monitoring device of the user of an impending illness.

2. The non-transitory computer program product of claim 1, wherein the local monitoring device of the user comprises a telecommunication device configured to analyze the sample of the speech input from the microphone to generate the voice quality information.

3. The non-transitory computer program product of claim 1, wherein the respiration-vocalization state information comprises respiratory quality information associated with a sample of an aspiration input to a sensor, wherein the sensor is configured to be in fluid communication with a respiratory system of the user while the user is wearing a continuous positive airway pressure (CPAP) mask operably coupled to the local monitoring device of the user.

4. The non-transitory computer program product of claim 3, wherein the sensor comprises an air pressure sensor.

5. The non-transitory computer program product of claim 3, wherein the sensor comprises an air flow sensor.

6. The non-transitory computer program product of claim 3, wherein the respiratory quality information comprises a frequency and an amplitude of one or more respiratory disturbance events during a selected time period.

7. The non-transitory computer program product of claim 1, wherein the environmental quality data comprises published regional air quality data.

8. The non-transitory computer program product of claim 1, wherein the known sensitivities data comprises the other users' allergy information and the other users' vocalization-respiration state information for normal and allergic responses.

9. The non-transitory computer program product of claim 1, wherein the at least one statistical relationship value comprises a correlation coefficient.

10. The non-transitory computer program product of claim 1, further comprising operation of:

iteratively updating the at least one statistical relationship value upon receiving additional data containing additional respiration-vocalization state information associated with the local monitoring device of the user.

11. The non-transitory computer program product of claim 1, wherein the respiration-vocalization state information is associated with a first time property, wherein the known sensitivities data is associated with a second time property, wherein the confidence indication is further based on a time period associated with the first time property and the second time property.

12. A computer-implemented method comprising:

receiving data comprising respiration-vocalization state information and a first location property associated with a local monitoring device of a user;

in response to receiving the data, storing, in a data storage system, at least one record corresponding to the data;

accessing environmental quality data pertaining to a predetermined location in proximity to the user;

accessing known sensitivities data comprising information associated with other users with known irritant sensitivities and a second location property;

determining at least one statistical relationship value representative of a statistical relationship between the at least one record, the environmental quality data, and the known sensitivities data based on the first location property, the predetermined location, and the second location property via a data correlation engine, wherein the at least one statistical relationship value is associated with a confidence indication that is based at least in part on a proximity level associated with the first location property and the second location property;

storing, in the data storage system, the at least one statistical relationship value in association with the at least one record;

wherein the respiration-vocalization state information comprises voice quality information associated with a sample of speech input of the user received at a microphone of the local monitoring device to create baseline data of the user's voice;

automatically activating a respiration-vocalization data acquisition system whenever the user employs his voice to interact with the local monitoring device;

periodically sampling the speech input in order to determine a shift in the voice quality above a threshold level; and triggering an indicator, based on the determination that the shift in the voice quality is above the threshold level and based on the stored baseline data of the user's voice, wherein the baseline data includes at least one of tone, frequency and shift of the user's voice, wherein the indicator alerts the local monitoring device of the user of an impending illness.

13. The computer-implemented method of claim 12, wherein the local monitoring device of the user comprises a telecommunication device configured to analyze the sample of the speech input from the microphone to generate the voice quality information.

14. The computer-implemented method of claim 12, wherein the respiration-vocalization state information comprises respiratory quality information associated with a sample of an aspiration input to a sensor, wherein the sensor is configured to be in fluid communication with a respiratory system of the user while the user is wearing a continuous positive airway pressure (CPAP) mask operably coupled to the local monitoring device of the user.

15. The computer-implemented method of claim 14, wherein the sensor comprises an air pressure sensor.

16. The computer-implemented method of claim 14, wherein the sensor comprises an air flow sensor.

17. The computer-implemented method of claim 14, wherein the respiratory quality information comprises a frequency and an amplitude of one or more respiratory disturbance events during a selected time period.

18. The computer-implemented method of claim 12, wherein the environmental quality data comprises published regional air quality data.

19. The computer-implemented method of claim 12, wherein the respiration-vocalization state information is associated with a first time property, wherein the known sensitivities data is associated with a second time property, wherein the confidence indication is further based on a time period associated with the first time property and the second time property.

20. An apparatus comprising at least one processor and at least one non-transitory memory comprising program code, the at least one non-transitory memory and the program code configured to, with the at least one processor, cause the apparatus to at least:
  receive data comprising respiration-vocalization state information and a first location property associated with a local monitoring device of a user;
  in response to receiving the data, store, in a data storage system, at least one record corresponding to the data;
  access environmental quality data pertaining to a predetermined location in proximity to the user;
  access known sensitivities data comprising information associated with other users with known irritant sensitivities and a second location property;
  determine at least one statistical relationship value representative of a statistical relationship between the at least one record, the environmental quality data, and the known sensitivities data based on the first location property, the predetermined location, and the second location property via a data correlation engine, wherein the at least one statistical relationship value is associated with a confidence indication that is based at least in part on a proximity level associated with the first location property and the second location property;
  store, in the data storage system, the at least one statistical relationship value in association with the at least one record;
  wherein the respiration-vocalization state information comprises voice quality information associated with a sample of speech input of the user received at a microphone of the local monitoring device to create baseline data of the user's voice;
  automatically activate a respiration-vocalization data acquisition system whenever the user employs his voice to interact with the local monitoring device;
  periodically sampling the speech input in order to determine a shift in the voice quality above a threshold level; and
  triggering an indicator, based on the determination that the shift in the voice quality is above the threshold level and based on the stored baseline data of the user's voice, wherein the baseline data includes at least one of tone, frequency and shift of the user's voice, wherein the indicator alerts the local monitoring device of the user of an impending illness.

\* \* \* \* \*